United States Patent
Williams et al.

(10) Patent No.: US 6,370,421 B1
(45) Date of Patent: Apr. 9, 2002

(54) DENSITY MODULATED CATHETER FOR USE IN FLUOROSCOPY BASED 3-D NEURAL NAVIGATION

(75) Inventors: James Williams, Princeton Junction; Arun Krishnan, Plainsboro; Ali Bani-Hashemi, Belle Meade, all of NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/607,901

(22) Filed: Jun. 30, 2000

(51) Int. Cl.[7] ............................................. A61M 25/00
(52) U.S. Cl. ...................... 600/433; 600/435; 600/424; 604/528; 604/529
(58) Field of Search .................. 600/424, 425, 600/427, 431, 433, 435; 378/42; 382/130; 604/529, 528

(56) References Cited

U.S. PATENT DOCUMENTS 6,036,682 A * 3/2000 Lange et al. ................ 604/264
6,285,903 B1 * 9/2001 Rosenthal et al. .......... 600/424

* cited by examiner

Primary Examiner—Marvin M. Lateef
Assistant Examiner—Runa Shah Qaderi
(74) Attorney, Agent, or Firm—Donald B. Paschburg (57) ABSTRACT

A method and apparatus for providing a high-quality representation of a volume having a real-time 3-D reconstruction therein of movement of a catheter, wherein its real-time movement is determined using a lower-quality representation of only a portion of the volume. Movement of the catheter is detected in a 2-D X-ray fluoroscopy image and is reconstructed in a 3-D angiography (X-ray) reconstruction. Described is a catheter design for easier detection, and a technique for 3-D reconstruction of a catheter from real-time 2-D fluoroscopic images and stored 3-D angiography data, so as to present the 3-D reconstructed catheter in the common coordinate frame.

12 Claims, 7 Drawing Sheets

PROJECTION (FLUORO) IMAGE

FIG. 4

PROJECTION (FLUORO) IMAGE

DENSITY MODULATED CATHETER FOR USE IN FLUOROSCOPY BASED 3-D NEURAL NAVIGATION

BACKGROUND

1. Field of the Invention

The present invention relates to a density modulate catheter for use in a high-quality representation of a volume, wherein the real-time movement of the catheter is determined using a lower-quality representation of a portion of the volume.

2. Background of the Invention

3-D angiography is a relatively new application of an X-ray interventional procedure that utilizes a rotational run of an X-ray apparatus to acquire a series of 2-D X-ray projections along a circular (or almost circular) orbit. The rotational run is acquired by moving an X-ray source and an Image Intensifier (II camera mounted on a rotatable C-arm about a patient, while a continuous injection of contrast bolus is administered into the vasculature of the patient. The rotational series of 2-D image data is then sent to a cone beam reconstruction process, which generates a 3-D reconstruction of the patient's vascular structure.

The vascular structures depicted in the 3-D reconstructed images are then studied by the clinicians in order to plan an interventional procedure (operation). Once the plan is determined, catheters are used to carry out what is called an endovascular procedure. The entire procedure is constantly monitored by the clinicians under the guidance of a 2-D fluoroscopic imaging procedure. The 2-D fluoroscopic imaging procedure uses the same imaging apparatus and patient positioning as was used to perform the 3-D angiography procedure. Before starting the intervention, the clinician studies the previously acquired 3-D vasculature structures in order to choose an optimum way to place the C-arm to generate the best 2-D fluoroscopic image, thereby maximizing the ability of the 2-D procedure to aid in guiding the catheters during the operation.

Accordingly, the X-ray fluoroscopic image is used as a navigation tool by the clinicians to aid maneuvering the catheters through tortuous paths of the patient's vasculature. Every once-in-a-while the clinicians must inject contrast material to opacity the vessel, so that the vessel can be seen under the 2-D fluoroscopic imaging procedure. It is also common current practice to capture and store a contrast-enhanced fluoroscopic image, and then subtract that image from subsequent images. This results in a static display of the vascular structures (displayed in white), while the live (real-time) catheter appears in black This procedure is known as "road mapping". The roadmap is a 2-D projection of the vascular structures, and like any 2-D projection of a 3-D body has substantial positional ambiguity.

It is an object of the present invention to provide a more accurate real-time representation of the movement of an object in a volume when a previously acquired high-quality static representation of the volume is available but only a lower-quality real-time representation is available for detecting movement of the object. In this regard, it is an object of the present invention to develop a real-time high-quality 3-D representation of the movement of a catheter in the brain of a patient.

It is a further object of the present invention to present the real-time movement of the catheter in three dimensions to a doctor performing a neurosurgical procedure.

An even further aspect of the invention is the design of a new catheter for facilitating detection of the catheter.

In this regard, once coordinate transformations are determined, a novel interactive real-time image visualization is provided which merges the stored 3-D representations of the volume with a real-time 3-D reconstruction of the detected movement of the object.

SUMMARY OF THE INVENTION

Described is an intensity modulated device for use and easy detection in fluoroscopy based 3-D neural navigation. The inventive device comprises a catheter containing an X-ray opaque material deposited on its outside surface along its length. The X-ray material has an X-ray absorption coefficient that varies along the length of the catheter. As a result, when one X-ray image is subtracted from another X-ray image, high intensity changes with respect to the catheter appear in a subtracted image.

BRIEF DESCRIPTION OF THE DRAWINGS

The present invention is illustrated in the figures of the accompanying drawings which are meant to be exemplary and not limiting, and in which like reference characters are intended to refer to like or corresponding parts.

DETAILED DESCRIPTION OF THE PREFERRED EMBODIMENTS

As a general overview, one aspect of the present invention includes 3-D reconstruction of arterial structures based on 2-D projections. Initially, a 3-D reconstruction of arterial tree is generated by injecting a contrast material or agent into a patient and taking a series of sequential 2-D projections around the patient. As an example, the 2-D projections are obtained in a substantially circular path around the patient, covering approximately 200-degree angle. Representatively, the number of 2-D projections may be collected on the order of 50, 80, or 130 depending on a protocol. It is understood, of course, that the present invention is not limited to the exact number of projections.

A tomographic reconstruction is then carried out on the obtained 2-D projections to generate a 3-D arterial tree of the patient. That is, a number of projections in the 2-D modality are used to obtain 3-D reconstruction data. The 3-D reconstruction data is represented in x, y, z coordinate frame and is pre-stored for subsequent us in a catheter navigation mode.

In the catheter navigation mode, the 3-D reconstruction data of the arterial tree is merged with a 2-D image taken by an X-ray source in a fluoroscopic mode (fluoroscopy). Fluoroscopy is an X-ray procedure, primarily used to visualize the motion of internal structures and fluids (dynamic images displayed on fluoroscopic screen or television monitor). During fluoroscopy, an operator views a continuous image of the motion of internal structures while the X-ray tube is energized. In this mode, X-ray intensity is reduced to a low level of radiation, and the resulting image appears very noisy, lacking clear contours. Although the resulting image is fuzzy, it is advantageously produced in real- time.

If a catheter moving through the patient can be detected (in accordance with one aspect of the is present invention), the same geometry used for obtaining the 3-D reconstruction data and 2-D fluoroscopic data allows real-time 3-D image reconstruction for display on the fluoroscopic screen or television monitor. Since the catheter is moving through a vessel, the catheter must actually lie in 3-D space, somewhere on a "sheath" which is a surface formed by taking a line (a catheter) and keep sweeping along the length of the catheter. This generates a surface, and the catheter can be anywhere on that surface. Since we know that the catheter is moving through the vessel, which is a 3-D structure, the intersection of this surface with the pre-stored 3-D reconstruction data gives you the location of the catheter.

By detecting the catheter in 2-D, using the pre-stored 3-D reconstruction of the arterial tree, and knowing the space within which the 3-D reconstruction data is represented with respect to the geometry of the X-ray device, we can provide a real-time 3-D rendering of the arterial structure for display on the monitor device.

The present invention is described in a preferred embodiment using a 3-D angiography apparatus, although the use of other devices which provide a representation of a volume are contemplated, such as a magnetic resonance imaging device or a computed tomography device.

To achieve these goals, in the illustrated preferred embodiment, the following components are needed:

1. A practical method for detecting the catheter from the real-time X-ray fluoroscopic sequences.
2. A method that combines the detected catheter from 2-D X-ray fluoroscopic images with the 3-D reconstructed structures to reconstruct the 3-D-catheter.
3. An interactive visualization that merges image data representative of the 3-D reconstructed catheter with the image data representative of the 3-D vasculature of the patient, and which allows the user to freely view the merged image data from any direction. This will be an advantage over the current 2-D X-ray fluoroscopy interventional technique, which forces the user to see a 2-D view of the volume from one viewpoint only.

Images from other medical modalities may also be merged with the above-described reconstructed representation to further enhance the information pool. For example, previously acquired 3-D MR acquisitions (different MR protocols, such as MR-angiography, spectroscopy, function, etc.) can be co-registered with the 3-D angiography data. The 3-D location and orientation of the catheter tip may be used to select or sample a region (such as a small planar patch or a volumetric block) from the MR volume. This information may be merged with the 3-D angiography data using a common visualization framework (i.e., coordinate system). This will enhance the ability of the physician to make better decisions. This type of image data merging is not limited to MR, and data representative of other medical imaging modalities can be used as well.

1. The X-ray Projection Model

Figure 1:
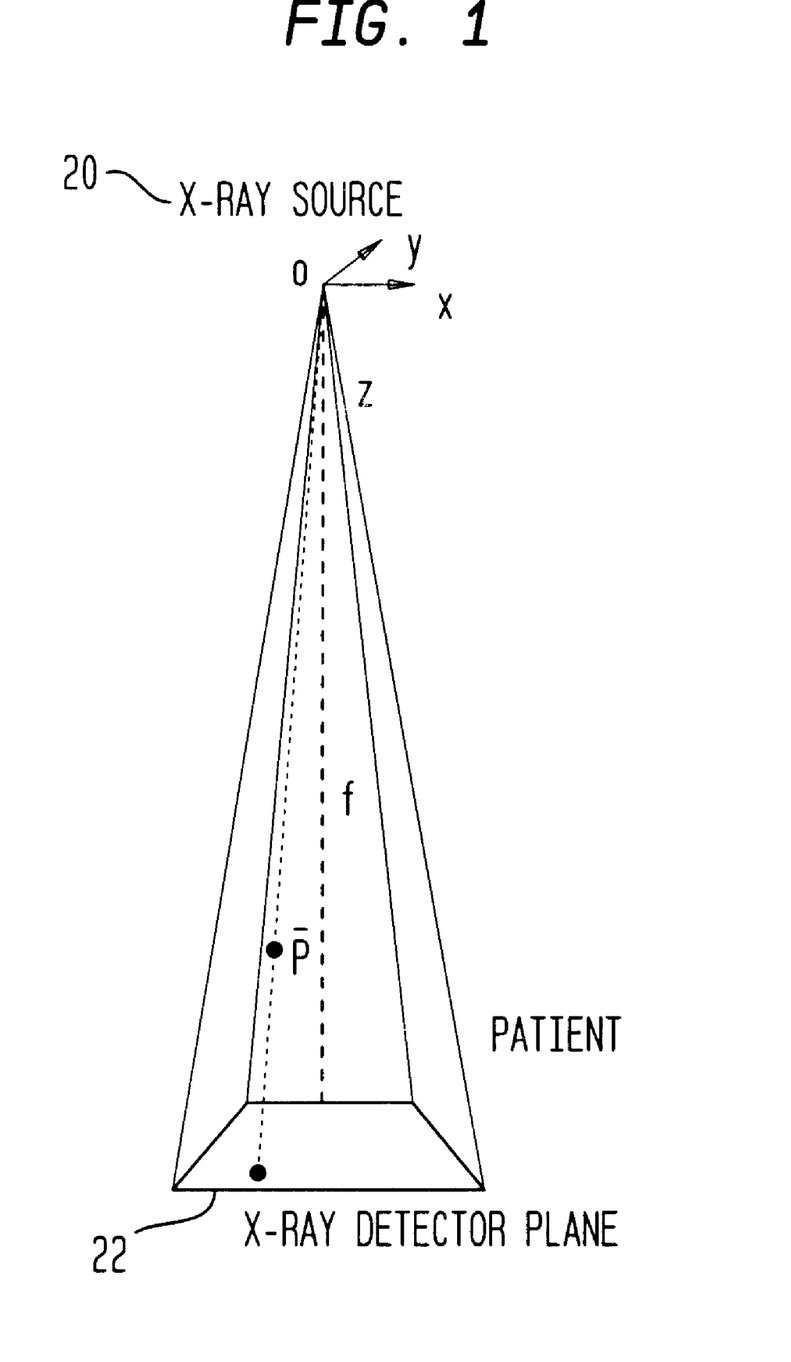
FIG. 1 is a schematic illustration of the X-Ray projection model.

FIG. 1 illustrates our projection model, wherein center 0 of the coordinate frame is at an X-ray source 20. The Z axis (the principal axis) is directed from X-ray source 0 perpendicular to an X-ray detector plane 22. The intersection of the principal axis Z with the X-ray detector plane 22 is defined to be the image center c. The X and Y axes are parallel to the image plane, i.e. comprise column and row vectors (respectively) which form an image coordinate frame on the detector plane 22. The distance from X-ray source 0 to the X-ray detector plane 22 is the focal length $f$.

The radiograph projection of a point $\vec{P}$ is a point $\vec{p}$ on the X-ray detector plane 22. Connecting a ray from X-ray source 0 to the 3-D point $\vec{P}$ and continuing until the ray intersects the X-ray detector plane 22 defines the projection point $\vec{p}$.

2. 3-D Reconstruction of the Catheter

As described above, interventional procedures are always performed under X-ray fluoroscopic guidance (with the exception of new interventional MR and CT-fluoroscopy, and ultrasound). The X-ray fluoroscopic image is a noisy (low signal-to-noise ratio) two-dimensional image, which depicts a radiographic projection of a volume of a patient, comprising:

1. the organs of the patient,
2. the catheter, and
3. the vascular structures in that patient, when a contrast medium is injected therein.

Figure 2:
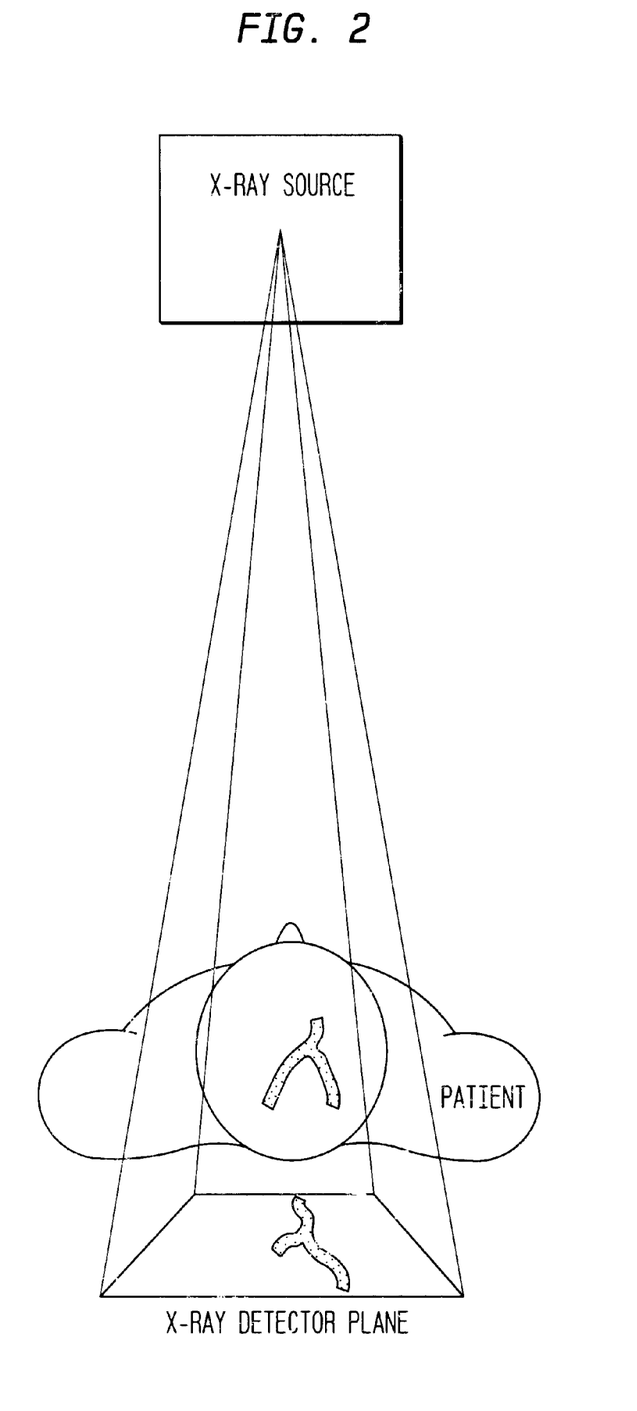
FIG. 2 is a schematic illustration of the X-ray projection geometry used to form a 2-D fluoroscopic image.
Figure 3:
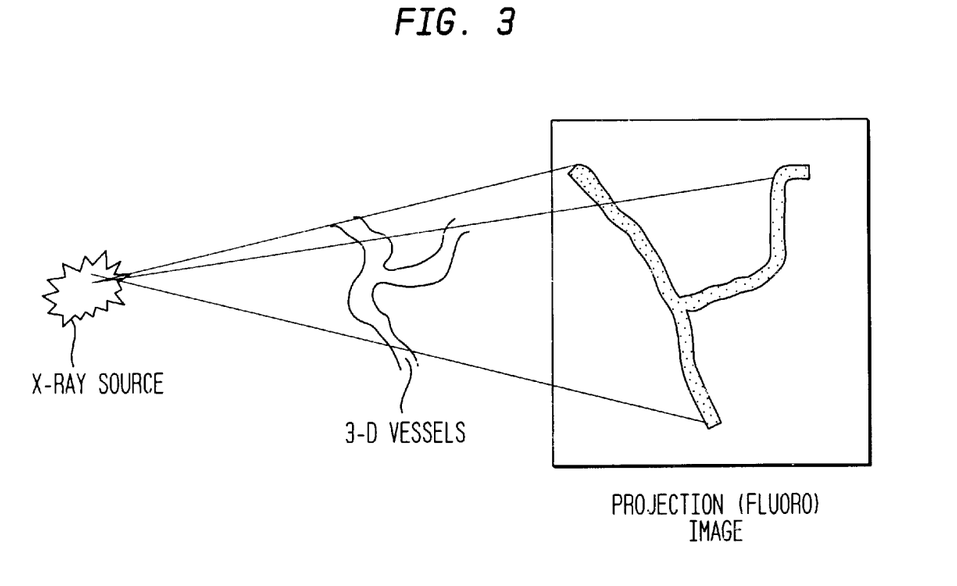
FIG. 3 is a schematic illustration of the X-ray projection of 3-D vessels to form a 2-D fluoroscopic image.

FIGS. 2 and 3 illustrate the X-ray projection geometry used to form the 2-D fluoroscopic image. The three-dimensional organs and the catheter undergo a 3-D to 2-D projection. As shown in FIG. 3, an X-ray source emits x-rays at 3-D vessels, resulting in a 2-D projection (fluoroscopic) image.

If a point is localized in two images taken from different but known projection angles, its position can be accurately determined in 3-D space. However, if a point is localized in only one 2-D image, its 3-D position may lie anywhere on a line connecting the point on the image plane with the X-ray source.

Figure 4:
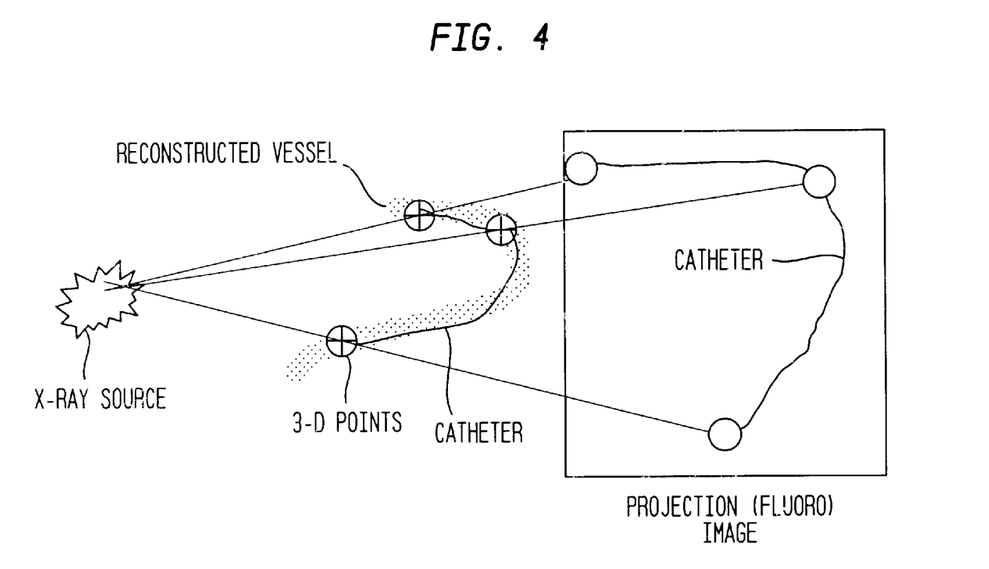
FIG. 4 is a schematic illustration of the 3-D catheter localization from a single view using reconstructed vasculature.

Given that the catheter can be segmented in a single 2-D projection image, the 3-D position of the catheter can be constrained to pass through a set of projecting lines in 3-D space. These projecting lines are shown in FIG. 4.

Given that the catheter must lie inside a vessel, the reconstructed vasculature is intersected with the projecting lines. The intersection of these lines and the reconstructed vasculature yields a 3-D locus of points. The paths (in most cases only one is feasible) are displayed to the user in a 3-D rendered display. Once a path is determined, it is updated incrementally as the catheter is moved.

To summarize, the 3-D reconstruction of the catheter from a single 2-D fluoroscopic image is, in general, ambiguous. However, we know that the catheter must physically lie within the vessels. If the 3-D reconstruction of the vessels is known (i.e. from the 3-D angiography reconstruction), the position of the catheter is also known since it is confined within the reconstructed vessels. This increases the certainty of the 3-D reconstruction of the catheter from a single 2-D view.

The accuracy with which, the catheter location can be determined depends on the size of the vessels. The thinner the vessels, the more closely confined is the catheter therebetween, and the more precisely the location of the catheter can be determined.

In this embodiment of the invention, we assume that the catheter can be reliably detected from the real-time 2-D fluoroscopic image sequence. In an alternative embodiment, some other imaging modality may be used. The catheter in the 2-D fluoroscopic image is represented by its centerline. The following section explains techniques useful for detecting a catheter from 2-D X-ray fluoroscopic images.

3. Use of 3-D Angiography for Catheter Reconstruction

This section describes a method and apparatus for 3-D reconstruction and visualization of the catheter using the 3-D angiographic representations of the volume. Due to the nature of the procedure, it is given that the catheter is confined to move within the vascular structures. Furthermore, the result of the 3-D angiography is 3-D (volumetric) data having large values where there is a vessel. Voxels that are outside of the vessels appear dark (low voxel intensities).

Figure 5:
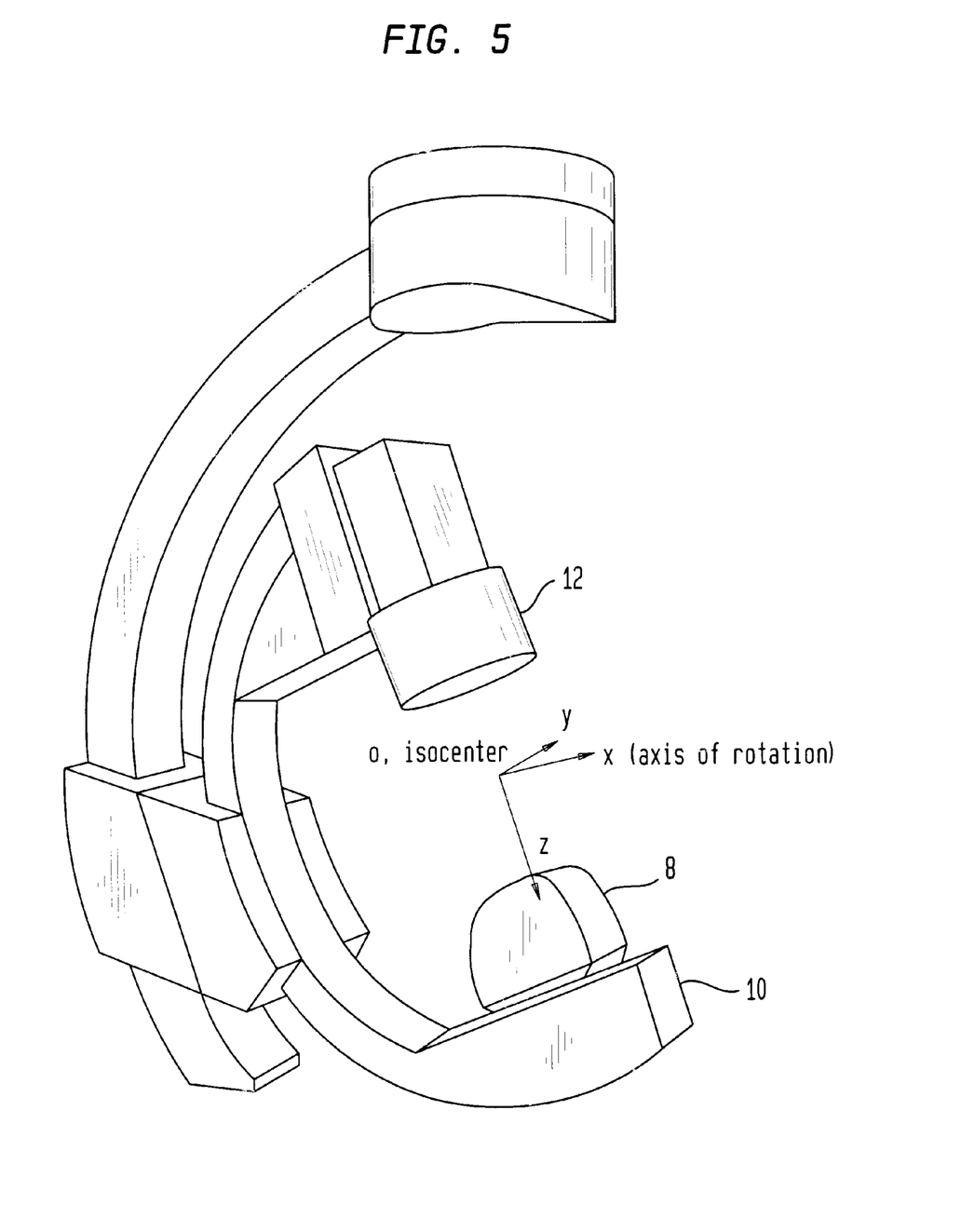
FIG. 5 is a schematic illustration of a C-arm gantry with the isocentric coordinate frame constructed in accordance with an embodiment of the present invention.

FIG. 5 is a schematic illustration of an imaging system constructed in accordance with an embodiment of the present invention. A C-arm 12 carries an X-ray source 8 and an image intensifier 10 in an orbit (for example, a circular path) around a patient. As known to those skilled in the art, X-ray image is a radiographic projection of an object onto a plane. It may be considered as a two-dimensional function of x and y such that at each point (x, y) it records the aggregate of all the absorptions along the ray emanating from the X-ray source to the point (x, y) on the image plane.

As shown in FIG. 5, the 3-D angiographic data is acquired by rotating a C-arm gantry of an X-ray device (such as Angiostar, Neurostar, and Multistar, manufactured and sold by Siemens Medical Systems, Inc. Iselin, N.J., USA) about its isocenter with the patient present. The C-arm does not necessarily follow a circular orbit, due to mechanical instabilities and sag. However, an effective isocenter may be computed for the C-arm. The 3-D angiography data is represented in such an isocentric coordinate framework. This framework is inherent in the C-arm gantry of the X-ray device, as shown in FIG. 3.

It is possible to represent the C-arm movements and positions in this isocentric coordinate frame. In clinical settings, the movements of the C-arm are commonly represented in the cranial-caudal, LAO-RAO frame. For example, the clinicians specify the position of the C-arm in cranial-caudal, LAO-RAO frame to acquire an optimum view for X-ray fluoroscopy. These two coordinate frames are attached to the same physical device, and one can easily convert from one coordinate to the other.

This means that we can specify geometry associated with and used to acquire the X-ray fluoroscopic image, in the space of 3-D angiography reconstruction.

Figure 6A:
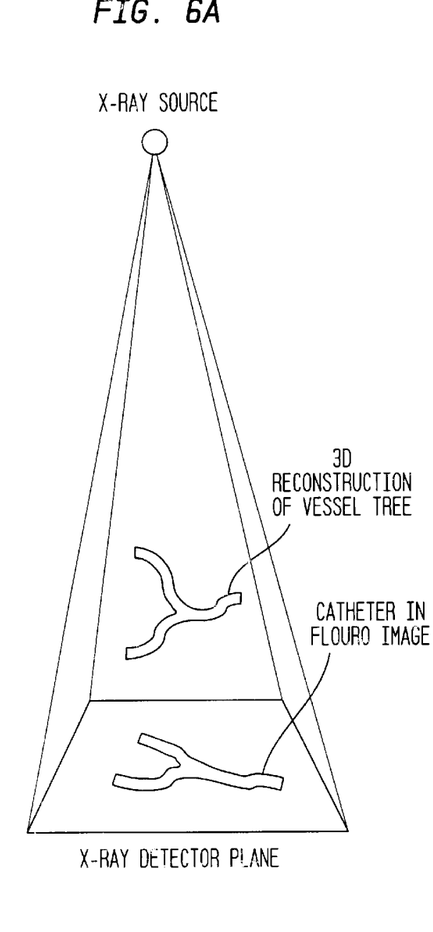
FIG. 6A is a schematic illustration of the catheter in the fluoroscopic image.
Figure 6B:
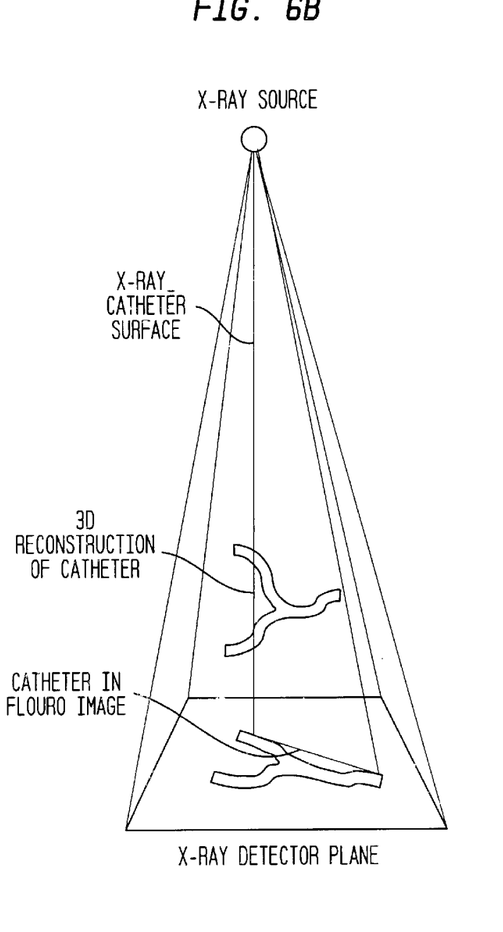
FIG. 6B is a schematic illustration of the reconstructed 3-D catheter using 3-D reconstructed vessels.

FIG. 6A illustrates the position of the detected catheter in the fluoroscopic image, and FIG. 6B is a schematic illustration of the reconstructed 3-D catheter using 3-D reconstructed vessels. The detected catheter is represented by its centerline, which is a thin planar curve in the image. Let's represent the catheter centerline in the image by the 2-D curve $\vec{c}(t)$ where, $$\vec{c}(t) = \begin{bmatrix} c_x(t) \\ c_y(t) \\ f \end{bmatrix} \text{ For } t \in (0, 1).$$

Connecting the X-ray source o to a point $\vec{c}(t)$ forms a ray $\vec{r}$. As t changes its value from 0→1, the ray $\vec{r}$ sweeps a surface s. Note that the actual 3-D catheter must:
1. lie on surface s, and
2. it must be inside the reconstructed vessels.

This implies that the 3-D reconstruction of the catheter must lie on the intersection of the surface s with the reconstructed volume (3-D vessels). The reconstructed volume may be converted into a probability, or a likelihood function, such that for every voxel it gives the likelihood of that voxel being a vessel. In that case, the intersection of the surface s with such a probability function gives the likelihood of the every point being a catheter.

To simplify the problem, we can create a binary volume by thresholding the reconstructed volume. This binary volume then determines if a voxel is vessel (non-zero) or not (zero). The intersection of the binary volume with the surface s will be non-zero where there is a possibility for the catheter to be present.

The reconstruction of the catheter is more complicated than described here. We need to apply knowledge and reasoning to disambiguate the 3-D reconstruction of the catheter. It suffices to say that the catheter position in 3-D may be computed with some remaining uncertainty.

4. Detection of Catheter from X-ray Fluoroscopic Sequences

The projection of the, catheter and the organs are all superimposed on the fluoroscopic image. This makes the detection of the catheter difficult. We propose a catheter design that lends itself to automatic detection from the 2-D fluoroscopic image.

We propose making a catheter, whose X-ray absorption coefficient varies along its length in a known and predefined manner. We call this intensity-modulated catheter. The advantage of such design is detectability under motion. One can continually subtract one image in the fluoroscopic sequence from the next (or later) images. One of the image subtraction techniques is commonly referred to as digital subtraction angiography (DSA). If the catheter continues moving, this results in high intensity changes in the subtracted image sequence. More elaborate techniques could be used, but that is not the focus of this document.

Figure 7A:
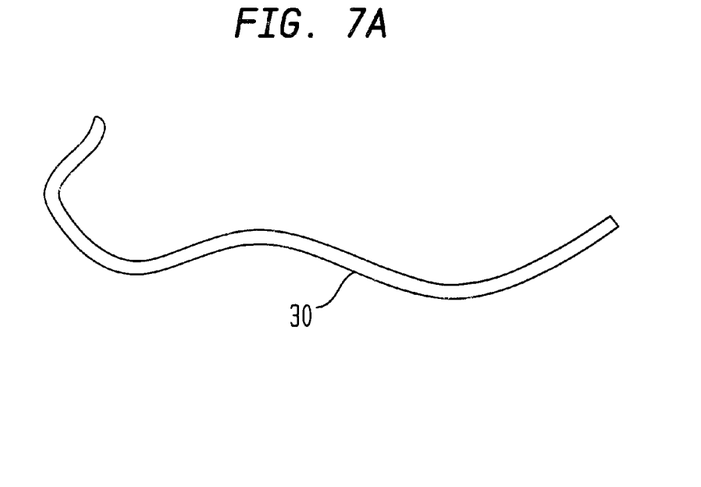
FIG. 7A is a schematic illustration of a representative intensity modulated catheter.
Figure 7B:
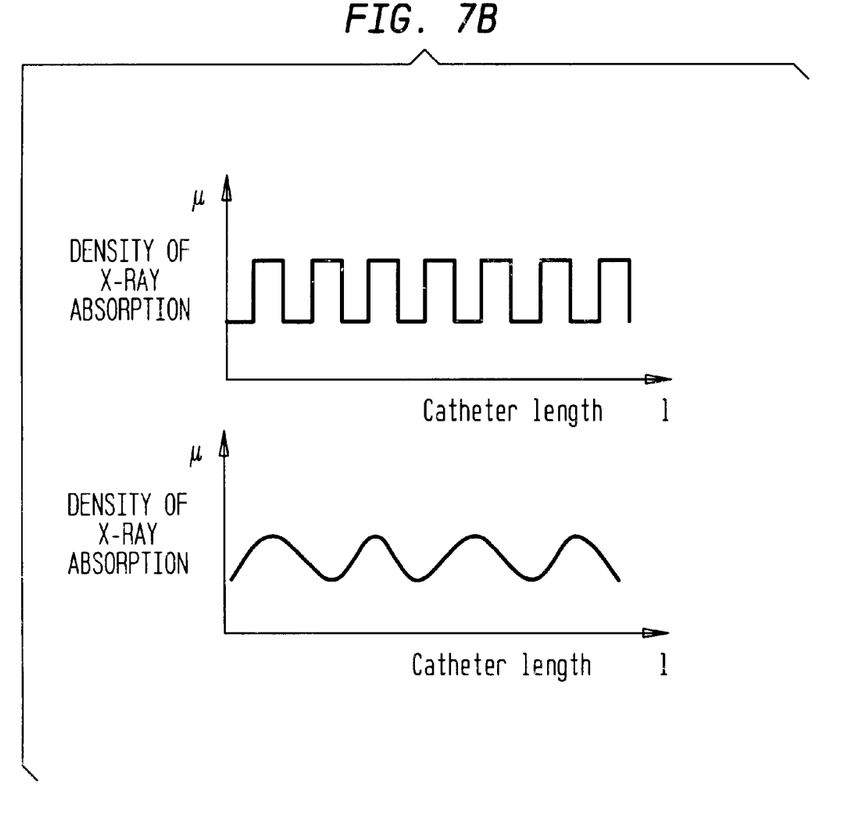
FIG. 7B is a schematic illustration of representative intensity modulations.

FIG. 7A schematically illustrates a representative intensity modulated catheter. The intensity modulation may have different forms. In FIG. 7B, a pulsed waveform and a sinusoidal waveform are schematically illustrated. When difference images are calculated, each waveform manifests different characteristics. A pulse shaped waveform will have large intensities near the edges, while a continuously varying waveform (such as sinusoidal) will have values everywhere.

The catheter can be encoded with special patterns, such as barcode, which would lend itself to easy identification under X-ray projection. Hence, the waveform used to modulate the intensity would actually be a code. The code may be designed such that its information remains unchanged due to X-ray projection. This design would have the advantage that we could identify which part of the catheter we are looking at (for example, a tip).

Figure 8A:
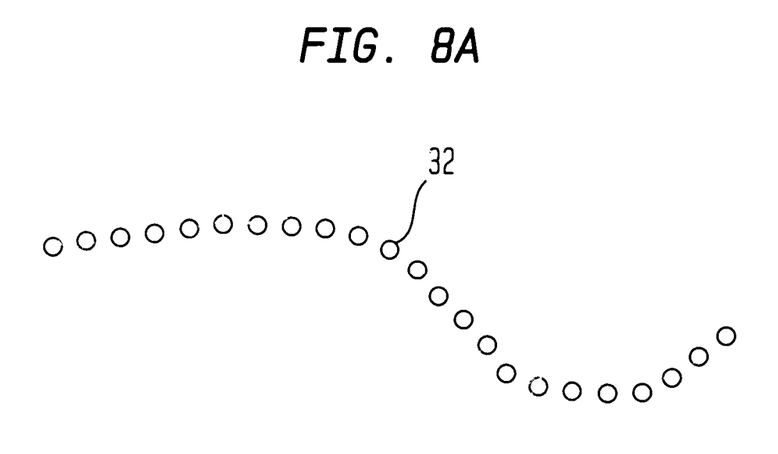
FIG. 8A is a schematic illustration of a representative intensity modulated catheter with a unique pattern of X-ray opaque rings or spheres.
Figure 8B:
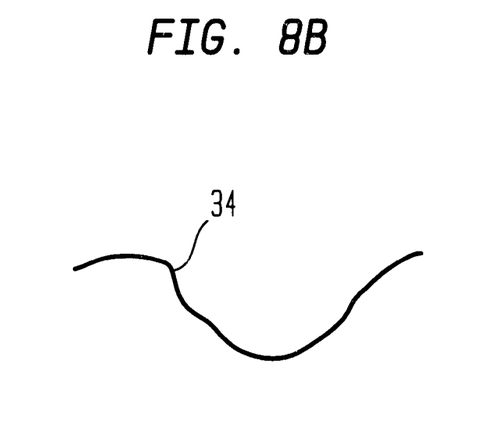
FIG. 8B is a schematic illustration of a spline for interpolating multiple points resulting from the unique pattern design of the catheter.

Another representative pattern may be a plurality of X-ray opaque rings or spheres embedded along the length of a catheter 32, as shown in FIG. 8A. The catheter with such pattern is easier to localize for the following reasons. An alternating pattern of light and dark can be segmented from the background by progressing subtraction. As the catheter moves, the subtraction of successive images will continue to produce an alternating dark/light pattern. In addition, unique sections of the pattern can be correlated in multiple views to isolate multiple points on the catheter in 3-D space. Given material properties of the catheter, a spline 34, as shown in FIG. 8B, simulating these material properties can be used to interpolate the points and provide a complete 3-D view of the catheter.

5. 3-D (Catheter Fusion with 3-D Angiography Images

3-D visualization techniques, such as interactive volume rendering are commonly used for viewing 3-D angiography data The position of the 3-D reconstructed catheter may be incorporated in the same visualization. This allows the user to view the catheter from arbitrary viewpoints.

All the catheter movements are presented in 3-D along with the 3-D vasculature. This simplifies the clinician's task for maneuvering the catheter through tortuous 3-D pathways of the cerebral arteries.

6. Registration and Fusion with other Modalities

The volume visualization is not limited to the 3-D angiography data. Images from other modalities, such as CT and MIR may be brought into the visualization. A pre-requisite for this is registration. Other modality images must first be registered with the 3-D angiography data. The other modality images must be brought into the same coordinate frame as C-arm gantry.

A basic CT scanning; apparatus for carrying out the method according to the present invention is well known in the art and generally comprises an X-ray tube and a radiation detector, mounted on a gantry for rotational movement about the body of a subject under study. As well known in the art, in order to generate an image of a body slice in interest, the X-ray tube projects X-ray beam through the subject. The attenuation of the X-ray beam is determined for a large number of paths through which X-ray beam slices through the subject. The radiation intensity is recorded by the detector for each slice beam. The detector is coupled to measurement electronics which codes the measurement values sensed by the detector. The measurement electronics is coupled to a computer which processes the coded measurement values and calculates a 3-D attenuation distribution. The attenuation distribution generally comprises a numerical matrix which is converted into an image that can be viewed by an operator.

As further known to those skilled in the art, in MR imaging magnetic field gradients are used in addition to a static magnetic field. Since the resonant frequency of the processing nuclei depends upon the precise magnetic field strength imposed upon it, the applied field gradients are used to provide a mechanism which encodes spatial information into the sensed frequency response signals. MR imaging devices correlate signal intensity at a given frequency with nucleus concentration and relaxation parameters at a given location. This provides spatial information which is used to make a map or image of the object, based upon signal intensity variations due to the concentration and/or relaxation time differences. Such techniques are routinely used to form MR medical diagnostic devices which provide two-dimensional (2-D) images. Many pulse and gradient sequence variations are also known which can be used to enhance the diagnostic value of the images produced.

One way of registration is to use the vessel structures in the 3-D angiography data as the basis for similarity with other modalities. As a representative embodiment of the present invention, let's focus our attention on the fusion with MR The following, outlines the steps needed to bring the two modalities of X-ray and MR together.

1. Place patient in the MR magnet with the head fixed (to prevent movement).
2. Acquire an MR-Angiography data set. This depicts the vascular structures (in lower resolution compared with 3-D angiography). This is used for registration with 3-D angiography images.
3. Acquire other MR protocols, such as fMRI (functional MRI, T1 or T2 weighted, etc.
4. Place the patient on the X-ray angiography table, and prepare him/her for neuroangiography.
5. Acquire a rotational run and reconstruct 3-D angiography data.
6. Use MR-Angiography and use the structural similarities (anatomical landmarks) with 3-D angiography image as the basis for registration. Transform the MR images so they are represented in the same coordinate frame as the 3-D angiography images (i.e. isocentric coordinate frame of the C-arm gantry).
7. Place the C-arm gantry in an optimum configuration for fluoroscopy.
8. Perform the endovascular procedures using the specially designed catheter (as described earlier). This is done under X-ray fluoroscopic imaging.
9. Detect the catheter and reconstruct it in 3-D.
10. Render the 3-D reconstructed catheter with the 3-D rendering of the Angiography data.
11. Use the 3-D location of the catheter tip and sample a sub-volume from the MR volume. This sub-volume could be a block or a plane in a well-defined orientation with respect to the catheter.
12. Render the MR sub-volume in the same space as the catheter and the 3-D angiography images.
13. As the catheter is moved, update the 3-D visualization.

The present invention enables the doctor to easily navigate in the three-dimensional space comprising the interior vessels of the patient. Advantages of the present invention include:

1. Less injection of contrast during the procedure (contrast material is considered harmful to patients, and it adds to the cost of the procedure).
2. Less X-ray dose to the patient and the clinical staff by reducing the procedure time.
3. The procedure time will be reduced and the safety of the procedure increased by eliminating guesswork and by providing decision support to control movement of the catheter.

Thus, there has been shown and described a novel fluoroscopy based 3-D neural navigation apparatus and method which satisfies all the objects and advantages sought therefore. Many changes, modifications, variations and other uses and applications of the subject invention will become apparent to those skilled in the art after considering this specification and its accompanying drawings, which disclose preferred embodiments thereof. All such changes, modification, variations and other uses and applications which do not depart from the spirit and scope of the invention are deemed to be covered by this patent, which is limited only by the claims which follow as interpreted in light of the foregoing description.

What is claimed is:

1. An intensity modulated device for use and easy detection in fluoroscopy based 3-D neural navigation, comprising:

a catheter containing an X-ray opaque material deposited along its length, wherein said X-ray material has an X-ray absorption coefficient that varies along the length of said catheter, such that when one X-ray image is subtracted from another X-ray image, high intensity changes with respect to said catheter appear in a resulting image wherein said catheter exhibits said high intensity changes depending on a shape of a radiographic waveform emitted by an X-ray device.

2. The device as claimed in claim 1, wherein said catheter exhibits said high intensity changes near edges if said radiographic waveform is pulse shaped.

3. The device as claimed in claim 1, wherein said catheter exhibits said high intensity changes continuously along its length if said radiographic waveform is sinusoidal.

4. The device as claimed in claim 1, wherein said catheter contains on its surface a pattern which provides easy identification of a portion of said catheter under X-ray projection.

5. The device according to claim 3, wherein said pattern is a plurality of bar codes spaced along a length of said catheter.

6. The device according to claim 3, wherein said pattern is a plurality of rings spaced along a length of said catheter.

7. A method for detecting; an intensity modulated catheter in a fluoroscopy based 3-D neural navigation, comprising:

depositing an X-ray opaque material along a length of said catheter, wherein said X-ray material has an X-ray absorption coefficient that varies along the length of said catheter; and subtracting one X-ray image from another X-ray image such that high intensity changes with respect to said catheter appear in a resulting image further comprising exhibiting said high intensity changes in a catheter image depending on a shape of a radiographic waveform emitted by an X-ray device.

8. The method as claimed in claim 6, further comprising exhibiting said high intensity changes near edges of said catheter image if said radiographic waveform is pulse shaped.

9. The method as claimed in claim 6, further comprising exhibiting said high intensity changes continuously along a length of said catheter image if said radiographic waveform is sinusoidal.

10. The method as claimed in claim 6, further comprising providing a pattern on a surface of said catheter which provides easy identification of a portion of said catheter under X-ray projection.

11. The method according to claim 8, wherein said pattern is a plurality of bar codes spaced along a length of said catheter.

12. The method according to claim 8, wherein said pattern is a plurality of rings spaced along a length of said catheter.

* * * * *